United States Patent [19]

Bujard et al.

[11] Patent Number: 4,868,111

[45] Date of Patent: Sep. 19, 1989

[54] GRAM-POSITIVE EXPRESSION CONTROL SEQUENCES

[75] Inventors: Hermann Bujard, Heidelberg, Fed. Rep. of Germany; Stuart Le Grice, Basel, Switzerland

[73] Assignee: Hoffmann-La Roche Inc., Nutley, N.J.

[21] Appl. No.: 875,437

[22] Filed: Jun. 17, 1986

[30] Foreign Application Priority Data

Jul. 5, 1985 [GB] United Kingdom ............... 8517071

[51] Int. Cl.[4] ............... C12P 21/00; C12N 15/00; C12N 1/20; C07H 15/12
[52] U.S. Cl. ............................. 435/68; 435/70; 435/91; 435/170; 435/172.3; 435/252.31; 435/252.33; 435/320; 435/832; 435/849; 536/27; 935/6; 935/8; 935/29; 935/39; 935/44; 935/61; 935/73; 935/74
[58] Field of Search ............. 435/68, 91, 172.1, 172.3, 435/170, 253, 822, 832, 839, 849, 320; 935/6, 8, 22, 23, 24, 27, 29, 38, 39, 44, 45, 47, 60, 72, 73, 74; 536/27

[56] References Cited

U.S. PATENT DOCUMENTS 4,495,280  1/1985  Bujard et al. ............... 435/6

OTHER PUBLICATIONS

Simons et al., 1984, Gene, 28: 55–64.
Nunberg et al., 1980, Cell, 19: 355–364.
Band et al., Gene 26: 313 (1983).
Briat et al., Proc. Natl. Acad. Sci. USA 81: 7373 (1984).
De Boer et al., Biochem. Soc. Symp. 48: 233 (1983).
Grange et al., Nucleic Acids Res. 12: 3585 (1984).
Hawley et al., Nucleic Acids Res. 11: 2237 (1983).
Jay et al., Proc. Natl. Acad. Sci. USA 81: 2290 (1984).
Moran, Jr. et al., Mol. Gen. Genet. 186: 339 (1982).
Zukowski et al., Proc. Natl. Acad. Sci. USA 80: 1101 (1983).
Brosius et al., J. Mol. Biol. 148: 107 (1981).
Dunn et al., Nucleic Acids Res. 8: 2119 (1980).
Ehrlich, S. D., Proc. Natl. Acad. Sci. USA 75: 1433 (1978).
Gilman et al., Nucleic Acids Res. 9: 5991 (1981).
Gryczan et al., J. Bacteriol. 134: 318 (1978).
Kreft et al., Molec. Gen. Genet. 162: 59 (1978).
Lee et al., Molec. Gen. Genet. 180: 57 (1980).
Lee et al., J. Mol. Biol. 139:407 (1980).
McLaughlin et al., J. Biol. Chem. 256:11283 (1981).
Michel et al., Gene 12:147 (1980).
Moran, Jr. et al., Cell 25:783 (1981).
Moran, Jr. et al., Nucleic Acids Res. 9:5979 (1981).
Murray et al., J. Biol. Chem. 257: 1053 (1982).
Rosenberg et al., Proc. Natl. Acad. Sci. USA 73:717 (1976).
Schoner et al., Gene 22:47 (1983).
Stueber et al., EMBO J. 3:3143 (1984).

*Primary Examiner*—Thomas G. Wiseman
*Assistant Examiner*—Richard C. Peet
*Attorney, Agent, or Firm*—Jon S. Saxe; George M. Gould; Norman C. Dulak

[57] ABSTRACT

New gram-positive expression control DNA sequences useful in the expression of pro- or eukaryotic proteins in gram-positive organisms are provided having in the downstream direction of transcription a transcription initiation DNA sequence of gram-negative origin combined with a ribosome binding site-encoding DNA sequence, optionally a foreign gene and a transcription termination sequence. Also described are expression vectors containing these expression control DNA sequences and processes using same for the manufacture of pro- and eukaryotic polypeptides. In addition processes for the manufacture of such gram-positive expression control DNA sequences and such expression vectors are described.

20 Claims, 10 Drawing Sheets

GRAM-POSITIVE EXPRESSION CONTROL SEQUENCES

TECHNICAL FIELD

The present invention relates to new gram-positive expression control DNA sequences, to expression vectors containing these DNA sequences, to host cells transformed with these expression vectors and to methods for producing pro- and eukaryotic proteins by using the new expression control DNA sequences, vectors and transformants.

BACKGROUND OF THE INVENTION

Most recombinant DNA work to date has been carried out with *Escherichia coli* (*E. coli*). *E. coli* is a member of the gram-negative class of bacteria which contain two layers of membranes enclosing a periplasmic space. Many of the products produced in *E. coli* are secreted into this periplasmic space, if secreted at all. Few products are secreted outside the living cells into the growth medium.

On the other hand, *Bacillus subtilis* (*B. subtilis*) is a member of the gram-positive class of bacteria which contain only a single layer of bacterial membrane. Thus *B. subtilis* can produce large amounts of protein which are secreted directly into the growth medium. Moreover, production of proteins in *B. subtilis* is advantageous since the organism is non-pathogenic and does not produce endotoxins. In addition, *B. subtilis* has been extensively studied and is the archetype for genetic studies among gram-positive microorganisms.

Although the general approach to gene cloning in *E. coli* is applicable to B. subtilis, attempts to produce a useful product of a heterologous gene cloned into *B. subtilis* and secreted into the growth medium have been retarded and made especially difficult because of the general lack of suitable cloning and expression vectors.

This paucity of expression vectors is explained in part by the lack of recognition of foreign transcription and translation initiation signals in *B. subtilis*. Consequently, the well known trp (Hallewell, R.A. and S. Emtage, Gene 9, 24-47 [1980]), lac (K. ItaKura et al., Science 198, 1056-1063 [1977]; Roberts, T.M. et al., Proc. Nat. Acad. Sci. USA 76, 5596-5600 [1979], lpp (Lee, N. et al., J. Bacteriol. 146, 861-866 [1981]; Zwiebel, L.J. et al., J. Bacteriol. 145, 654-656 [1981] and Natamura, K. and M. Inouye, Cell 18, 1109 [1979]) and bacteriophage λ $P_L$ (Bernard, H. et al., Gene 5, 59-76 [1979]) transcription and translation-directing systems are not functional in *B. subtilis*.

Thus, with the exception of a few drug resistance genes from gram-positive organisms such as staphylococcus and streptococcus, few foreign genes encoding prokaryotic and eukaryotic proteins have been expressed in Bacillus, especially *B. subtilis*, (for review see "Genetics and Biotechnology of Bacilli", eds. A. T. Ganesan and J. A. Hock; Academic Press, Inc. [1984] and dissertation of J. Palva,, infra). Moreover, the expression yield is in general small, and therefore the development of superior expression vectors having potent promoters for *Bacillus subtilis* has been desired.

At present, the known *Bacillus subtilis* promoters with the respective base sequences clarified include the veg promoter, tms promoter, pen P promoter (C.P. Moran Jr. et al., Mol. Gen. Genetics 186, 339-346 [1982]), spo VC promoter (C.P. Moran Jr. et al., Nucl. Acids Res. 9, 5979-5990 [1981]), spo VG promoter (C.P. Moran Jr. et al., Cell 25, 783-791 [1981]), φ 29 G3a promoter, O 29 G3b promoter, O 29 G2 promoter, O 29 A1 promoter (C.L. Murray and J.C. Rabinowitz, J. Biol. Chem. 257, 1053-1062 [1982]), pMG 102 promoter, pMG 201 promoter (M.Z. Gilman et al., Nucl. Acids Res. 9, 5991-6000 [1981]), spo 1-15 promoter (G. Lee et al., J. Mol. Biol. 139, 407-422 [1980]), spo 1-16 promoter (G. Lee et al., Molec. Gen. Genetics 180, 57-65 [1980]), and SPO2 promoter (R.G. Schoner et al., Gene 22, 47-57 [1983]). Among them, the SPO2 promoter (R.G. Schoner et al., supra) and the veg promoter (European patent application, publication no. 116411) are the only promoters that have actually been utilized in gene expression.

SUMMARY OF THE INVENTION

Under these circumstances, it is thus of advantage to develop more potent gene expression systems for use in gram-positive bacteria, e.g. Bacillus, particularly B. subtilis. In this respect, the versatile expression vectors of the present invention are particularly important because they allow for the first time the expression of genes encoding prokaryotic and eukaryotic proteins in Bacillus, especially B. subtilis, and other gram-positive host cells under the control of transcription initiation and termination DNA-sequences of gram-negative origin.

The present invention specifically provides gram-positive bacterial expression control DNA sequences comprising in the downstream direction of transcription a transcription initiation DNA sequence of gram-negative bacterial origin, a ribosome binding site-encoding DNA sequence of gram-positive or gram-negative bacterial origin optionally operatively linked to a foreign gene encoding prokaryotic or eukaryotic polypeptides, and a transcription termination DNA sequence of gram-negative or gram-positive bacterial origin. This invention also provides a process for the manufacture of such expression control DNA sequences, which process comprises combining in the downstream direction (5' to 3') a transcription initiation DNA sequence of gram-negative bacterial origin, a ribosome binding site-encoding DNA sequence of gram-positive or gram-negative origin, and a transcription termination DNA sequence of gram-negative or gram-positive bacterial origin to a functional unit by techniques of DNA recombination well-known in the art.

More precisely, the present invention allows the following combinations of: (a) a transcription initiation DNA sequence (promoter) of gram-negative bacterial origin with a ribosome binding site-encoding DNA sequence of gram-positive bacterial origin and a transcription termination DNA sequence of gram-negative bacterial origin, (b) a transcription initiation DNA sequence (promoter) of gram-negative bacterial origin with a ribosome binding site-encoding DNA sequence of gram-negative bacterial origin and a transcription termination DNA sequence of gram-negative bacterial origin, (c) a transcription initiation DNA sequence (promoter) of gram-negative bacterial origin with a ribosome binding site-encoding DNA sequence of gram-positive bacterial origin and a transcription termination DNA sequence of gram-positive bacterial origin, and (d) a transcription initiation DNA sequence (promoter) of gram-negative bacterial origin with a ribosome binding site-encoding DNA sequence of gram-negative bacterial origin and a transcription termination DNA sequence of gram-positive bacterial origin.

BRIEF DESCRIPTION OF THE FIGURES

The present invention will be better understood on the basis of the examples below when considered in connection with the following figures:

Restriction endonucleases have been abbreviated as follows:
E: EcoRI; Sm: SmaI; B: BamHI; S: SalI; P: PstI; H: HindIII; Xh: XhoI; X: XbaI; K: KpnI; Pv: PvuII; A: AccI: Sp: SphI; Bg: BglII; D: DraI;

In addition, the following abbreviations have been used:
kan: Structural gene for kanamycin nucleotidyl transferase;
cat: Structural gene for chloramphenicol acetyl transferase;
dhfr: Structural gene for mouse dihydrofolate reductase;
bla: Structural gene for beta lactamase;
CAT: Chloramphenicol Acetyl Transferase protein;
DHFR: Dihydrofolate Reductase protein;
ori+: Gram positive origin of replication;
ori−: Gram negative origin of replication;
SRBS: Portable ribosome Binding Site-encoding synthetic DNA sequence;
RBS: Ribosome Binding Site-encoding DNA sequence;
SD: Shine Dalgarno sequence;
$t_o$, T1, T2, T7: Transcriptional terminator to, T1, T2, T7; and
(H): Cohesive terminus of a HindIII which may be ligated to a HindIII terminus, without generating a HindIII site FIG. 1 Construction of the basic E. coli/B. subtilis shuttle vector p602/5, containing gram-positive (ori+) and gram-negative (ori−) origins of replication, together with drug resistance markers kanamycin (kan) and chloramphenicol. As such, this plasmid confers kanamycin resistance in both E. coli and B. subtilis. Chloramphenicol resistance is achieved through insertion of promoter-containing fragments between the EcoRI (E) and HindIII (H) sites. The E. coli cat gene presented here has its natural ribosome binding site-encoding DNA sequence.

Figure 2:
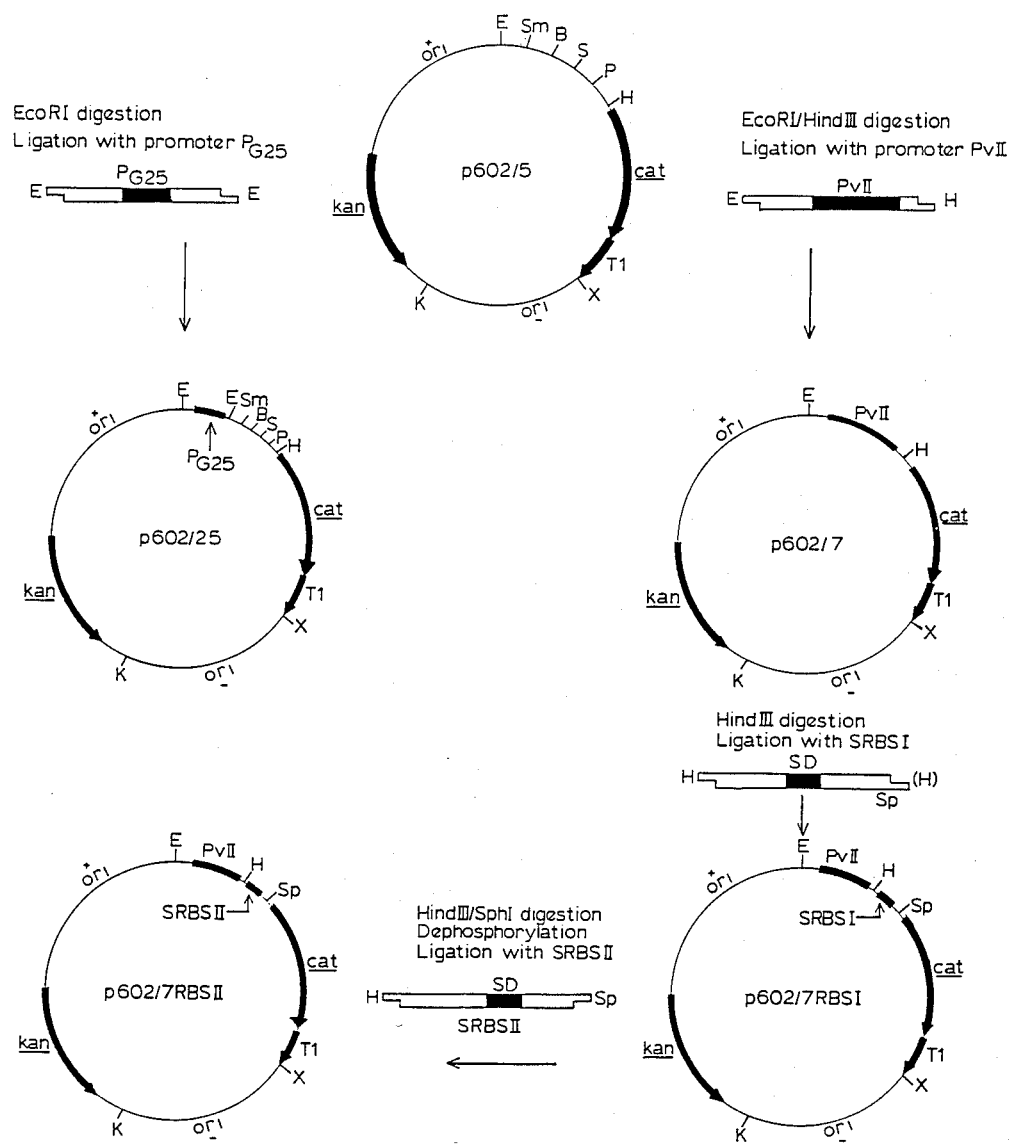

FIG. 2 Construction of the general expression vectors p602/7 and p602/25, together with the vectors p602/7RBSI and p602/7RBSII containing the ribosome binding site-encoding DNA sequences SRBSI or SRBSII. Insertion of the ribosome binding site-encoding DNA sequences SRBSI or SRBSII leads to the synthesis of two CAT-type proteins in E. coli, i.e., natural CAT protein from the wild type cat ribosomal binding site-encoding DNA sequence and an in-frame fusion CAT protein originating from SRBSI or SRBSII. In B. subtilis, a single fusion CAT protein is produced, originating from the ribosome binding site-encoding DNA sequences SRBSI or SRBSII. Plasmids p602/7, p602/25, p602/7RBSI and p602/7RBSII all confer chloramphenicol resistance in E. coli and B. subtilis.

Figure 3:
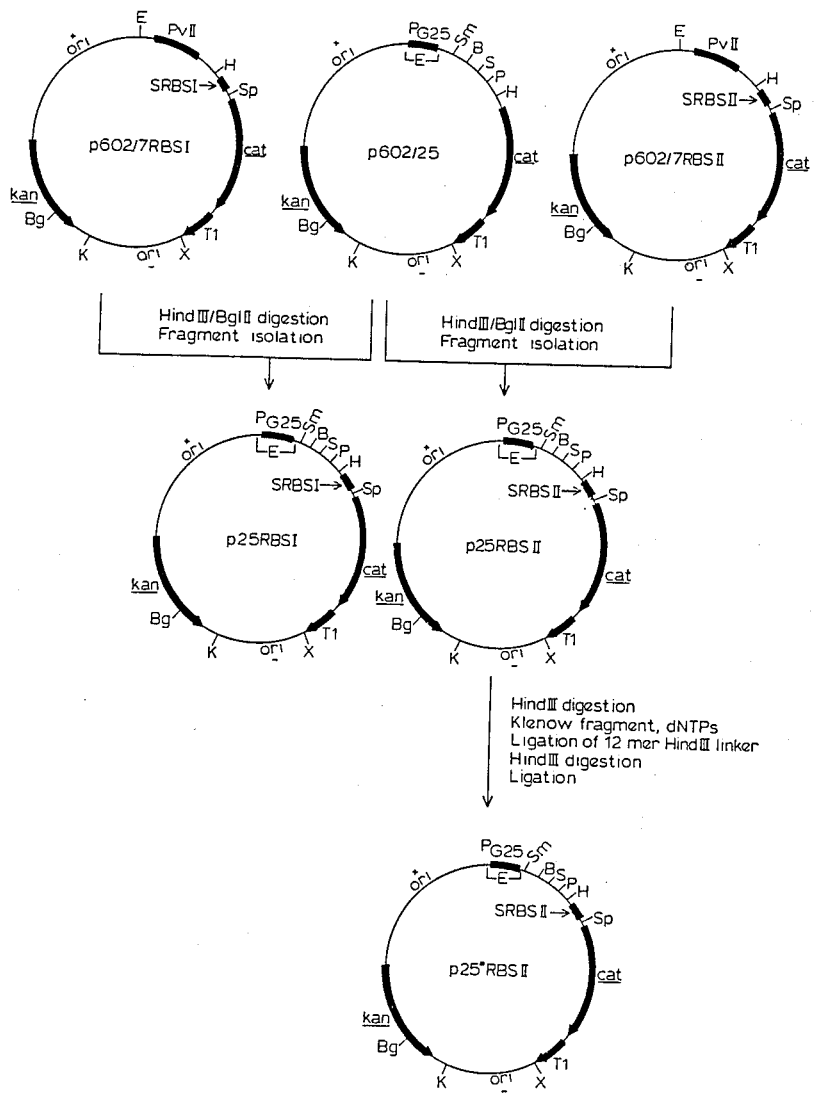

FIG. 3 Construction of vectors p25RBSI, p25RBSII and p25*RBSII containing the coliphage T5 promoter $P_G25$ combined with the ribosome binding site-encoding synthetic DNA sequences SRBSI or SRBSII. B. subtilis cells containing the vector p25RBSI synthesize a single CAT fusion protein, originating in the immediate downstream vicinity of SRBSI. B. subtilis cells containing the vector p25RBSII synthesize two fusion CAT proteins, originating at the immediate downstream vicinity of SRBSII, as well as a longer fusion protein originating from a ribosome binding site in the immediate vicinity of $P_G25$. Protein synthesis originating from this additional ribosome binding site was eliminated by providing a translational termination codon upstream from SRBSII, resulting in the vector p25*RBSII. Cells containing p25*RBSII now synthesize a single fusion CAT protein, originating from SRBSII.

Figure 4:
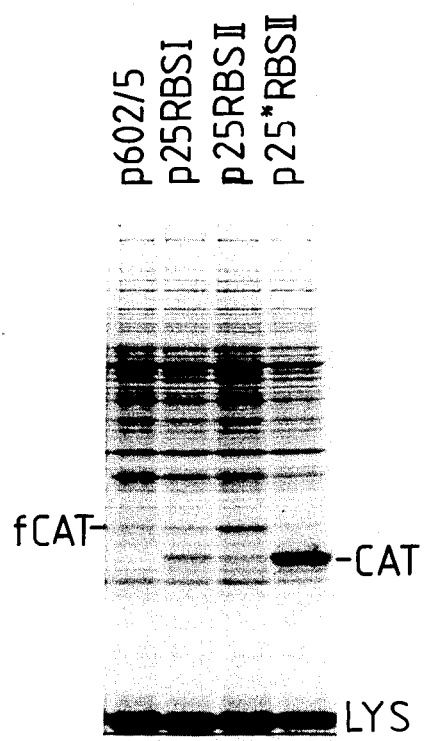

FIG. 4 Total proteins synthesized in B. subtilis strain BR151 containing the expression vectors p25RBSI, p25RBSII and p25*RBSII. The position of the CAT protein originating from SRBSI or SRBSII is indicated 'CAT'; the additional fusion CAT protein from cells harbouring p25RBSII is indicated 'f-CAT'. LYS indicates lysozyme, which is added externally to aid cell lysis.

Figure 5:
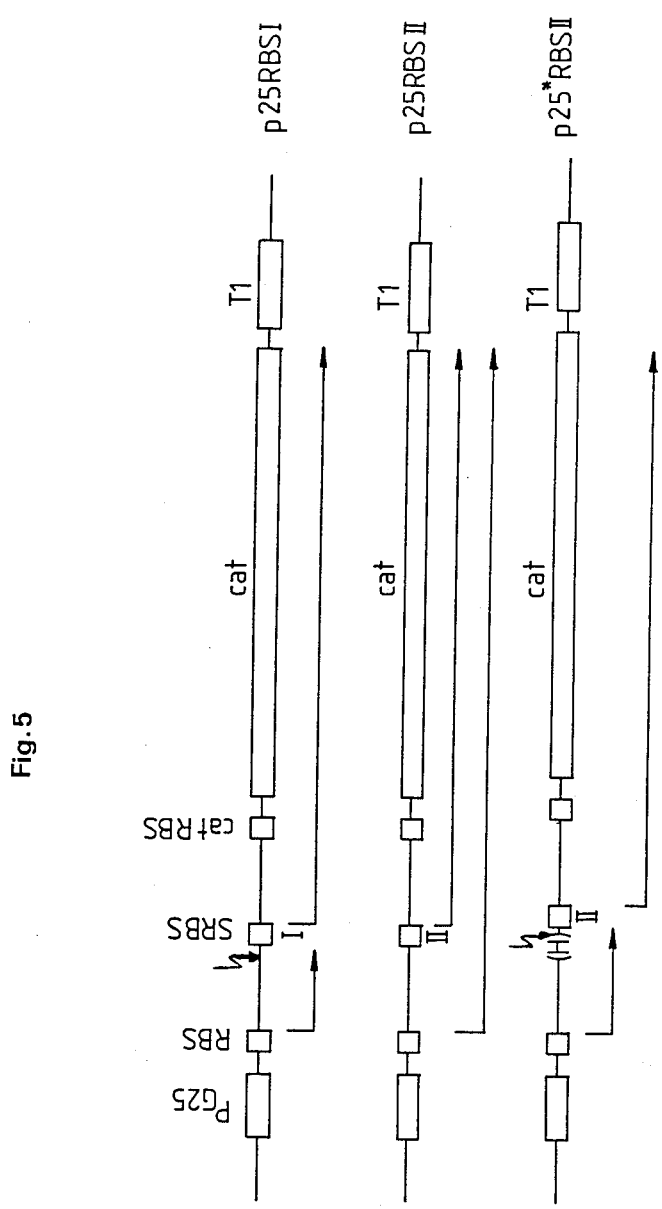

FIG. 5 Diagramatic representation of CAT proteins synthesized in B. subtilis containing the vectors p25RBSI, p25RBSII and p25*RBSII. An in-frame translational stop codon (٭) prevents read through protein synthesis into the cat gene from $P_G25$ RBS. Such an in-frame stop codon is absent in the construction p25RBSII; consequently, cat proteins arise from RBS and SRBSII. Modification of the HindIII site in p25*RBSII introduces an in-frame stop codon, and, as a consequence, yields a single CAT protein from SRBSII.

Figure 6A:
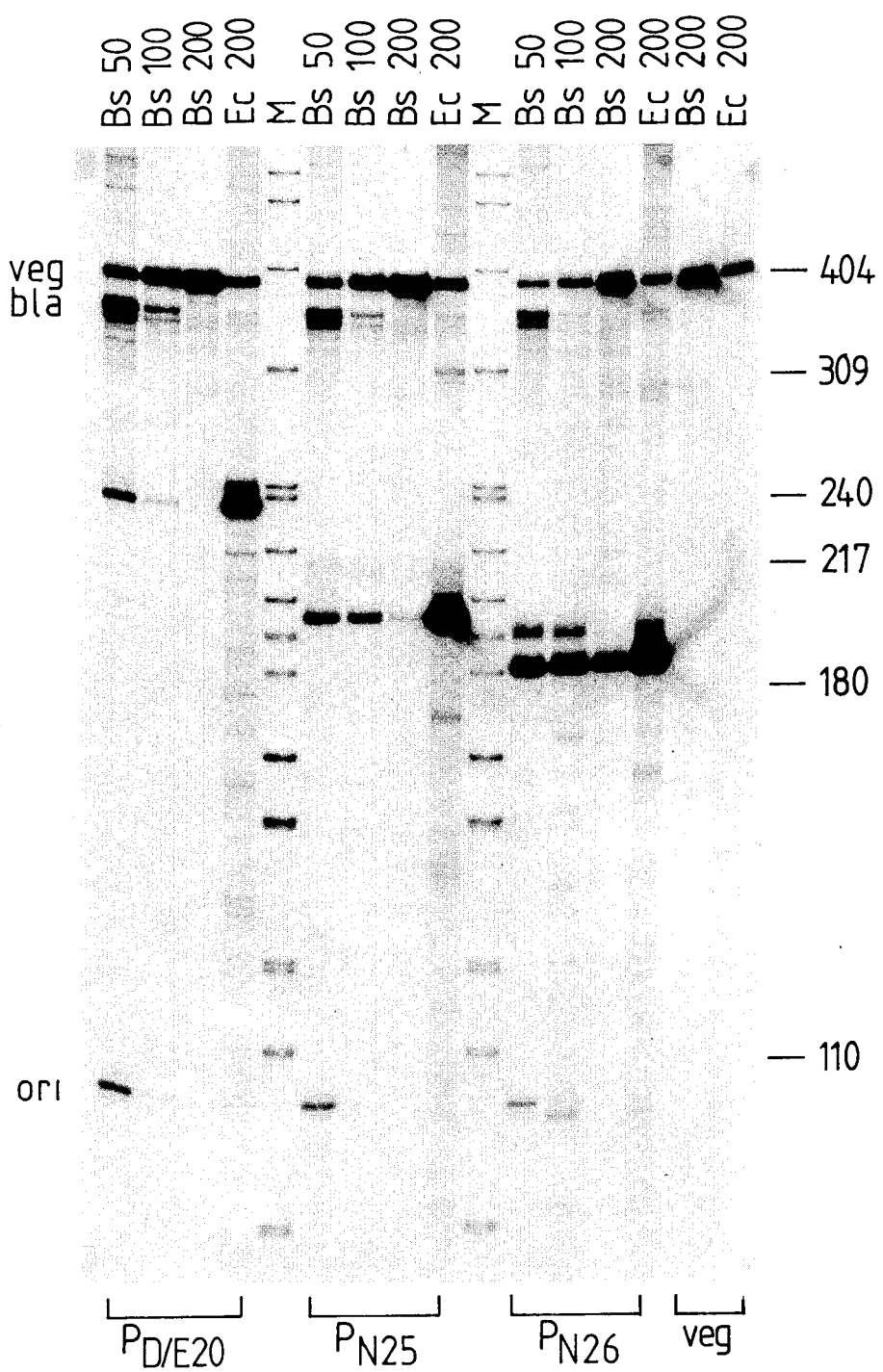
Figure 6B:
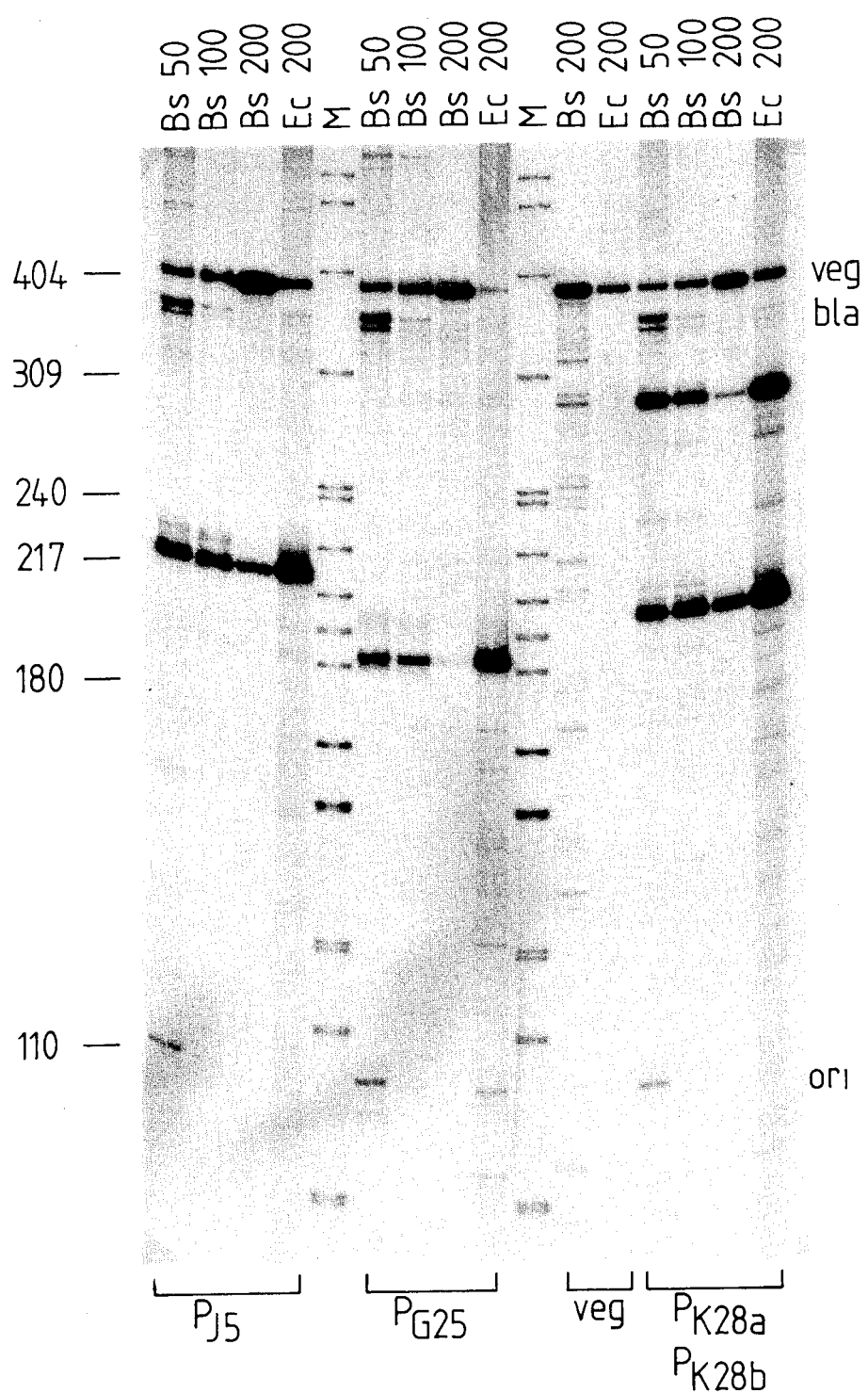

FIG. 6 In vitro transcriptional analysis of the promoters presented in Table 1. The notations 'Ec' and 'Bs' indicate analysis with E. coli and B. subtilis RNA polymerase, respectively, and the figures in conjunction with these notations give the salt concentration at which the transcription was performed. 'ori' and 'bla' transcripts arise from the vector into which the promoters were cloned. The panel indicated 'veg' represents transcription of solely the B. subtilis veg promoter (Le Grice, S. F. J. and Sonenshein, A. L. J. Mol.Biol., 162, 551–564, 1982). 'veg' indicated at the side of the panel indicates transcription of internally supplied veg promoter DNA. M, molecular weight marker, means HpaII-cleaved pBR322 DNA. Only the sizes of bands relevant to the present research have been presented. Note that the panel illustrating transcription from the T5 promoter $P_K28a/P_K28b$ has two new transcripts, as both promoters are present on a single restriction fragment.

Figure 7:
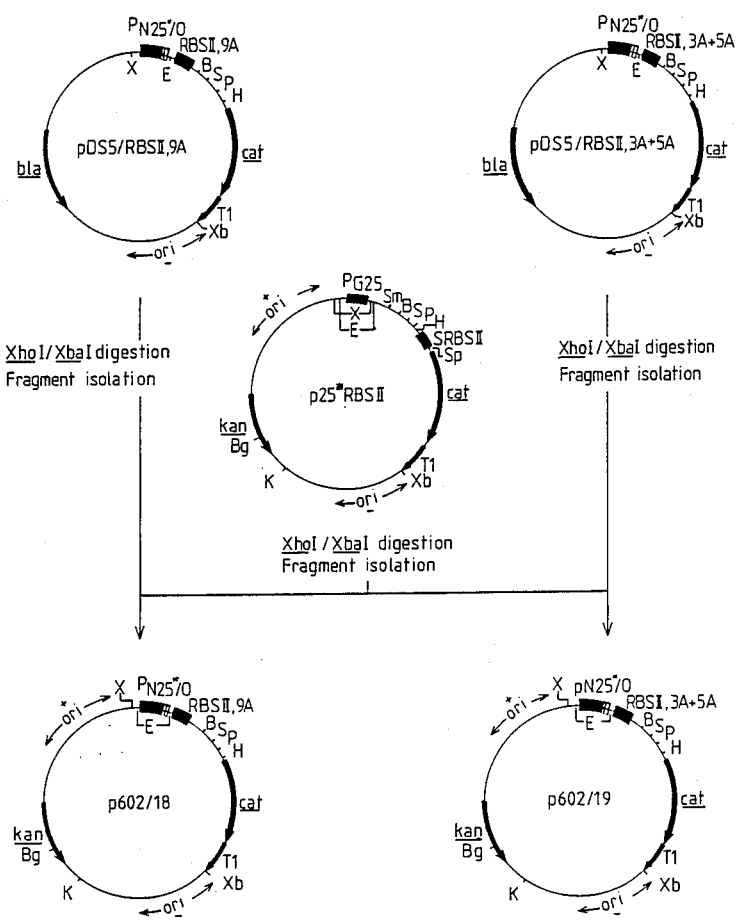

FIG. 7 Construction of the shuttle vectors p602/18 and p602/19, containing the coliphage T5 promoter $P_{N}25$ operably linked to either the the synthetic ribosome binding site-encoding DNA sequence RBSII, 9A (p602/18) or RBSII, 3A+5A (p602/19). Insertion of the synthetic ribosome binding site-DNA encoding sequences leads, in both cases, to synthesis of a fusion CAT protein initiating in the immediate vicinity of the synthetic ribosome binding site and terminating at the natural translational stop codon of the cat gene. Plasmids p602/18 and 602/19 both confer chloramphenicol resistance on *B. subtilis.*

Figure 8:
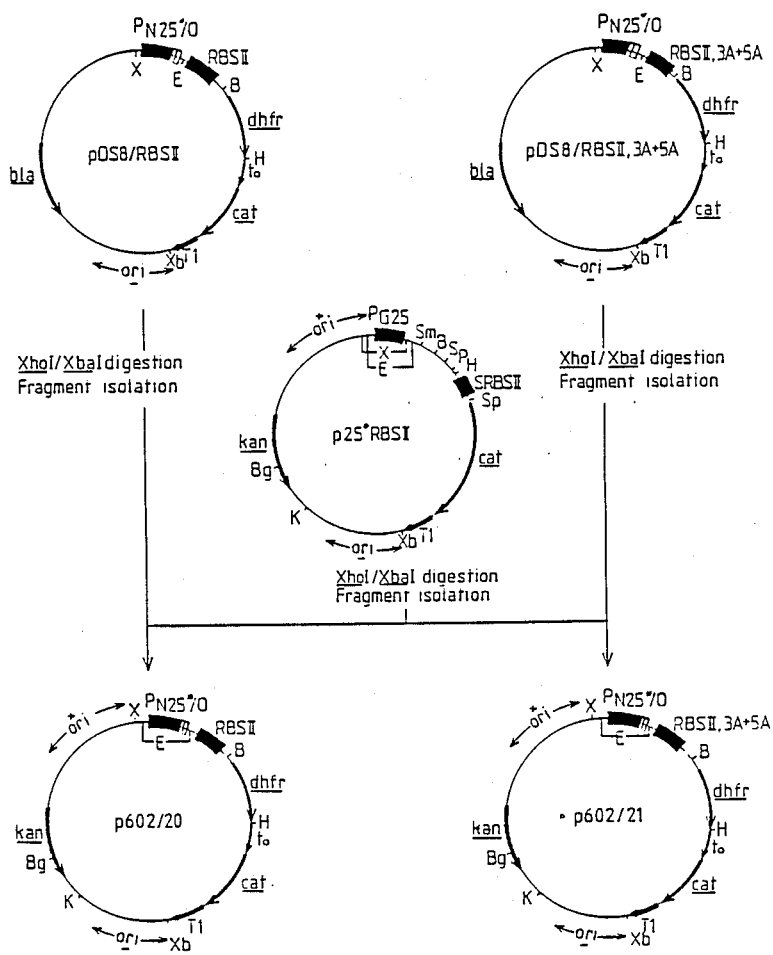

FIG. 8 Construction of the shuttle vectors p602/20 and p602/21, containing the coliphage T5 promoter $P_{N}25$ operably linked to the synthetic ribosome binding site-encoding DNA sequences RBSII (p602/20) or RBSII,3A+5A (p602/21). Insertion of the synthetic ribosome binding site-DNA encoding sequences leads, in both cases, to synthesis of a fusion DHFR protein, initiating in the immediate vicinity of the synthetic ribosome binding site and terminating at the natural translational termination codon of the dhfr gene. *B. subtilis* cells containing 602/20 or 602/21 are resistant to 10 μg/ml trimethoprim.

Figure 9:
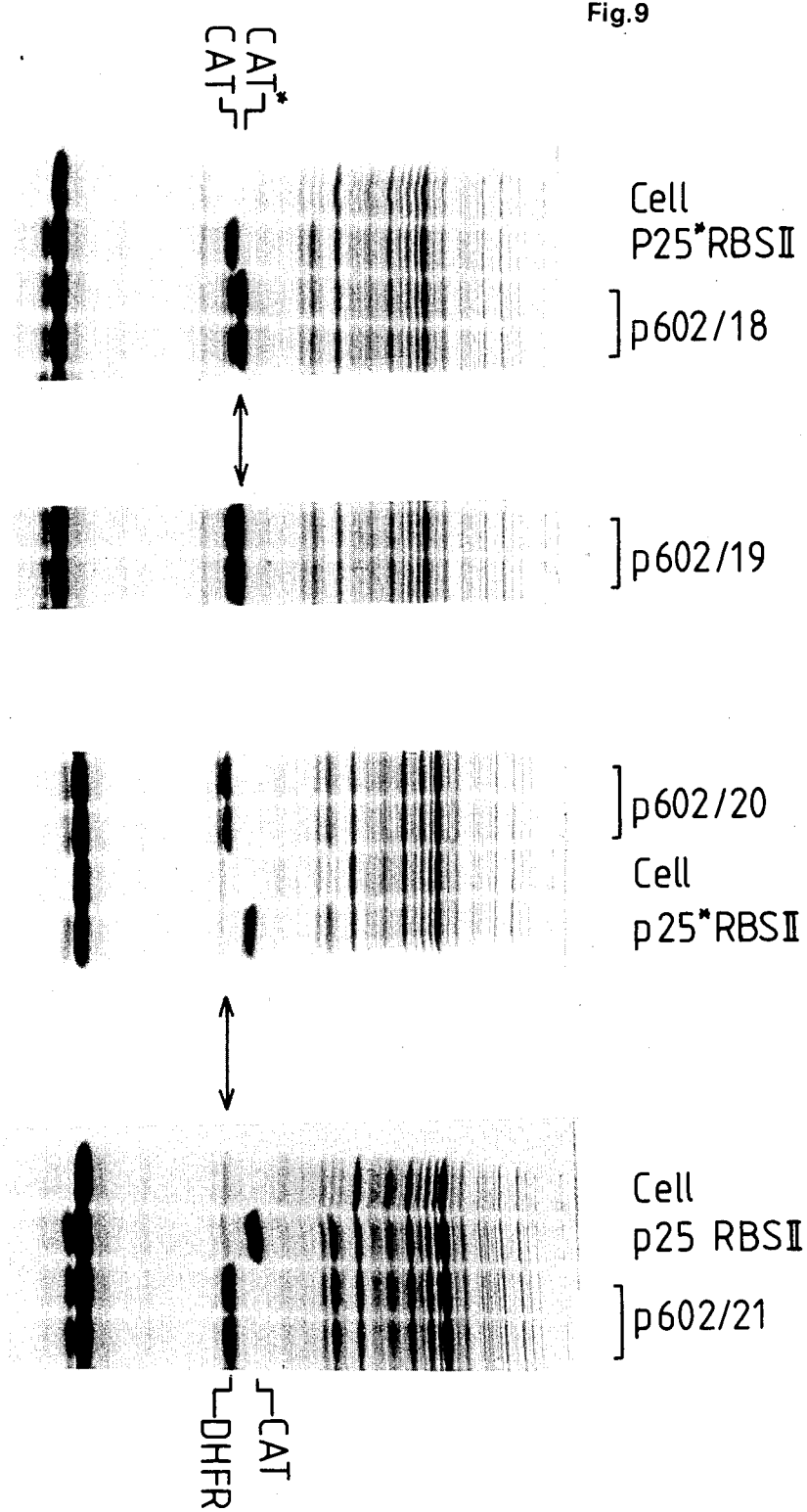

FIG. 9 Total proteins synthesised in *B. subtilis* strain BR151 containing the plasmids p602/18, p602/19, p602/20 and p602/21. 'Cell' denotes protein synthesis from plasmid-free cells. As a reference, CAT synthesis from p25*RBSII has been included. The positions of the fusion CAT protein CAT* (from p602/18 and p602/19) and fusion DHFR protein (from p602/20 and p602/21) have been indicated.

DESCRIPTION OF THE INVENTION

The term bacterial origin used in connection with transcription initiation DNA sequences comprises (a) naturally occurring bacterial transcription initiation sequences and functional variations thereof including substitutions or inversions of single or several nucleotides and repeats of such transcription initiation DNA sequences and (b) chemically synthesized (synthetic) transcription DNA sequences capable of initiating transcription in bacteria.

The term bacterial origin used in connection with ribosome binding site-encoding DNA sequences comprises (a) naturally occurring bacterial ribosome binding site-encoding DNA sequences and functional variations thereof including substitutions or inversions of single or several nucleo- tides and (b) chemically synthesized (synthetic) ribosome binding site-encoding DNA sequences capable of initiating translation in bacteria.

The term bacterial origin used in connection with transcription termination DNA sequences comprises (a) naturally occurring bacterial transcription termination DNA sequences and functional variations thereof including substitutions or inversions of single or several nucleotides and repeats of such transcription termination DNA sequences and (b) chemically synthesized (synthetic) transcription termination DNA sequences capable of terminating transcription in bacteria.

In a preferred application genes encoding prokaryotic or eukaryotic proteins can be expressed in Bacillus, particularly *B. subtilis,* and other gram-positive organisms under the transcriptional control of coliphage T5 or T7-derived promoters and *E. coli*-derived terminators.

In this invention T5 and T7 promoters are defined as promoter function-mediating DNA sequences occurring in genomes of the coliphage T5 and T7 family and functional combinations derived from such sequences.

T5 promoters useful in the present invention are those of the "preearly" "early" and "late" expression class of the phage, especially the sequences described in the dissertation of R. Gentz, Universität Heidelberg, 1984: $P_J5$, $P_N25$, $P_N26$, $P_{D/E}20$, $P_G5$, $P_G20$, $P_G22$, $P_G25$, $P_G28$, $P_K28a$, $P_K28b$.

The T7 promoters useful in the present invention include the "early" expression class of the phage, especially the promoters A1 and A2 (Hawley, D.K. and McClure, W.D., Nucleic Acids Res. 11, 2237–2255 [1983]).

The DNA sequences of some of the preferred T5 or T7 promoters mentioned above are indicated in Table I below:

TABLE I

```
           A:T Box          -35              -10
P_D/E 20   ACTGCAAAAAATAGT TTGACACCCTAGCCGATAGGCTT TAAGATGT ACCCAGTTCGATGA
P_N 25     TCATAAAAAATTTAT TTGCTTTCAGGAAAATTTTTCT GTATAAT AGATTCATAAATTTGA

P_N 26     ACTTAAAAATTTCAGT TGCTTAATCCTACAATTCTT GATATAAT ATTCTCATAGTTTGAA
P_J 5      ATATAAAAACCGTTA TTGACACAGGTGGAAATTT AGAATATACT GTTAGTAAACCTAATG    Phage T5

P_K 28a    TAGTTAAAATTGTAGT TGCTAAATGCTTAAATACTT GCTATAAT ATTTATATAAATTGAT
P_K 28b    ATTATAAAGTGGTTA TTGACATTTTCGCCGCTTAGGT ATATACT ATTATCATTCAGTTGA

P_G 25     AAAAATAAAAATTT CTTGATAAAATTTTCCAATACTAT TATAAT ATTGTTATTAAAGAGG
```

TABLE I-continued

```
T7A1  TTATCAAAAGAGT ATTGACT TAAAGTCT AACCT AT AGGATACTT ACAGCCAT CGAGAGG  ⎤
                  |      |  |                   ‾‾‾‾‾‾‾                   |
T7A2  CACGAAAAACAGGT ATTGACAACATGAAGT AACAT GCAGTAAGAT ACAAAT CGCT AGGT A ⎦  Phage T7
      |            | |    |
```

Table I shows the nucleotide sequence of the promoters used in the present invention. The sequence between −50 and +10 is presented, within which the −35 hexamers and upstream A:T-rich regions are boxed, while the −10 hexamers are overlined.

The ribosome binding site-encoding DNA sequence which is necessary for the initiation of translation in a host cell consists of (1) an ATG translation initiation codon for the amino acid methionine, (2) a sequence of 4 to 12 bases which are complementary to bases at the 3'-end of 16s ribosomal RNA and which is known as the Shine Dalgarno (SD) sequence and (3) a sequence of bases between these two known as the linker region.

The ribosome binding site-encoding DNA sequences used in the present invention and forming part of it may be provided by ribosome binding site-encoding sequences of gram-positive or gram-negative origin capable of functioning in Bacillus, particularly *B. subtilis*, and other gram-positive organisms, inclusive of several known ones (J.R. McLaughlin et al., J. Biol. Chem. 256, 11283-11291 [1981]; C.P. Moran Jr. et al., Mol. Gen. Genetics 186, 339-346 [1982]).

However the preferred ribosome binding site-encoding sequences used in this invention are portable ribosome binding site-encoding synthetic RNA sequences (SRBS) with the formula indicated in Table II below:

origin capable of functioning in Bacillus, particularly *B. subtilis*, and other gram-positive organisms. The preferred gram-negative terminators used in this invention include the *E. coli*-derived terminators $t_o$ (M. Rosenberg et al., Proc. Natl. Acad. Sci. U.S.A. 73, 717-721 [1976], T1, T2 (J. Brosius et al., J. Mol. Biol. 148, 107-127 [1981] and T7 (J.J. Dunn and Studier, F.W., Nucleic Acids Res. 8, 2119-2132 [1980].

The transcription initiation DNA sequences, the portable ribosome binding site-encoding sequences and the transcription termination sequences of the present invention can be obtained in accordance with methods well-known in DNA chemistry including total chemical synthesis of the respective DNA sequence, e.g., in a nucleotide synthesizer.

The invention further comprises expression vectors capable of directing expression of a gene encoding pro- and eukaryotic proteins in a bacillus, particularly *B. subtilis* or another gram-positive organism transformed therewith, containing (a) a gram-positive bacterial expression control DNA sequence having in the downstream direction of transcription the following units: at least one transcription initiation DNA sequence of gram-negative bacterial origin combined with a ribosome binding site encoding DNA sequence of gram-positive or gram-negative origin, optionally a foreign

TABLE II

```
SRBSI          5'                                              3'
                    AGCTTTATATAAGGAGGAGTTAAGCATGCAC
                       AATATATTCCTCCTCAATTCGTACGTGTCGA
               3'                                              5'

SRBSII         5'                                              3'
                    AGCTTGGATTTAAAATTTAGGAGGAATTTAAGCATG
                       ACCTAAATTTTAAATCCTCCTTAAATTC
               3'                                              5'

RBSII, 3A + 5A 5'                                              3'
                    AATTCATTAAAGAGGAGAAATTAACTATGAGGG
                        GTAATTTCTCCTCTTTAATTGATACTCCCCTAG
               3'                                              5'

RBSII          5'                                              3'
                    AATTCATTAAAGAGGAGAAATTAACTATGAGAG
                        GTAATTTCTCCTCTTTAATTGATACTCTCCTAG
               3'                                              5'

RBSII, 9A      5'                                              3'
                    AATTCATTAAAGAGGAGAAATTAACTATGGAAG
                        GTAATTTCTCCTCTTTAATTGATACCTTCCTAG
               3'                                              5'
```

These SRBSs have been constructed in a form so that they can function in conjunction with any desired gene encoding prokaryotic or eukaryotic polypeptides in Bacillus, particularly *B. subtilis*, and other gram-positive organisms. The ability to so function renders the SRBS "portable".

The transcription termination DNA sequence may be provided by terminators of gram-negative bacterial gene encoding prokaryotic or eukaryotic polypeptides and a transcription termination DNA sequence, (b) at least one vector origin of replication and (c) at least one antibiotic resistance gene as well as a process for the manufacture of such expression vectors.

The transcription initiation DNA sequence may be provided by a gram-negative promoter. The preferred gram-negative promoters used are coliphage T5 or coliphage T7 promoters with the formulae indicated in Table 1.

The origin of replication may be of gram-negative and/or gram-positive origin and thus the expression vectors can be employed as shuttle vectors (Ehrlich, S.D., Proc. Natl. Acad. Sci. U.S.A. 75, 1433-1436 [1978]; Kreft, J. et al., Molec. gen. Genet. 162, 59-67 [1978]; Michel, B. et al., Gene 12, 147-154 [1980]), which can replicate both in E. coli and Bacillus, especially B. subtilis. Preferred expression vectors using ribosome binding site-encoding synthetic DNA sequences ligated to a coliphage T5 promoter and capable of replicating both in E. coli and B. subtilis (shuttle vectors) are described in Examples 4, 5 and 7 to 10, infra.

The expression vectors of the present invention can be constructed using techniques of DNA recombination that are well known in the art (see laboratory manual "Molecular Cloning" by Maniatis et al., Cold Spring Harbor Laboratory, 1982) comprising the steps of:

(a) inserting into an existing cloning vector in the downstream direction of transcription at least one transcription initiation DNA sequence of gram-negative bacterial origin and a ribosome binding site-encoding DNA sequence of gram-positive or gram-negative bacterial origin, (b) providing in said cloning vector at least one restriction endonuclease site next to said ribosome binding site-encoding DNA sequence;

(c) inserting at least one foreign gene encoding prokaryotic or eukaryotic polypeptides into said restriction endonuclease site next to said ribosome binding siteencoding DNA sequence, and (d) inserting at least one transcription termination DNA sequence in the downstream direction of said foreign gene encoding prokaryotic or eukaryotic polypeptides.

The vector used to assemble the expression vectors of the present invention may be any convenient plasmid, cosmid, or phage capable of transforming and replicating itself in the host microorganisms. Plasmids suitable for cloning in B. subtilis and/or E. coli are mentioned, e.g., in the laboratoy manual "Molecular Cloning" by Maniatis et al., supra, and in the dissertation of J. Palva, University of Helsinki, 1983. Preferred vectors of plasmid origin used to assemble the expression vectors in this invention are pUB 110 (T.J. Gryczan et al., J. Bacteriol. 134, 318-329 [1978]), pDS 5 and pDS 6 (D. Stueber et al., EMBO J. 3, 3143-3148 [1984]).

Plasmids of the p602 and p25 families are specific examples of plasmidic shuttle vectors of the present invention. Their preparation is described in more detail in Examples 1 to 5 and 7 to 10. B. subtilis strains containing the especially preferred plasmids of the p25 family (B. subtilis BR151 transformed with p25RBSI; p25RBSII; p25*RBSII) were deposited at Deutsche Sammlung von Mikroorganismen (DSM) in Gottingen on June 20, 1985, the accession Nos. being DSM 3350, DSM 3351 and DSM 3352, respectively. B. subtilis strains containing the especially preferred plasmids of the p602 family (B. subtilis BR 151 transformed with p602/18; p602/19; p602/20; p602/21) were deposited at Deutsche Sammlung von Mikroorganismen (DSM) in Gottingen on May 14, 1986, the accession Nos. being DMS 3723, DSM 3724, DSM 3725 and DSM 3726, respectively.

Foreign genes that may be inserted into the expression vectors of this invention may be selected from a large variety of genes (DNA genes or DNA copies of RNA genes) that encode prokaryotic or eukaryotic polypeptides in vivo and in vitro. For example, such genes may encode enzymes, hormones, polypeptides with immuno-modulatory, anti-viral or anti-cancer properties, antibodies, antigens, and other useful polypeptides of prokaryotic or eukaryotic origin. The preferred foreign genes used in this invention are the genes encoding E. coli chloramphenicol acetyltransferase (cat) and mouse dihydrofolate reductase (dhfr).

Examples of proteins which can be expressed by using the improved expression control system of the present invention are dihydrofolate reductase, chloramphenicol acetyltransferase, malaria surface antigens, lymphokins like IL-2, interferons alpha, beta and gamma, insulin and insulin precursors, growth hormones, tissue plasminogen activator, human renin or HTLV-III proteins.

Methods for expressing genes encoding prokaryotic or eukaryotic proteins using the expression vectors, especially shuttle vectors, of this invention are well-known (Maniatis et al., supra). They include transforming an appropriate host with an expression vector having the desired DNA sequence operatively inserted into an expression control DNA sequence of the present invention, culturing the host under appropriate conditions of growth and isolating the desired polypeptide from the culture. Those of skill in the art may select from these known methods those that are most effective for a particular gene expression without departing from the scope of this invention.

The selection of a particular host for use in this invention is dependent upon a number of factors recognized by the art. These include, for example, compatability with the chosen expression vector, toxicity of the proteins encoded for by the hybrid plasmid, ease of recovery of the desired protein, expression characteristics, biosafety and costs. Within these general guidelines, examples of useful bacterial hosts are gram-negative and gram-positive bacteria, especially strains of E. coli and B. subtilis. The most preferred host cell of this invention is B. subtilis BR 151 (stocked at The Bacillus Genetic Stock Center under BGSC No. 1A40). However, other B. subtilis strains such as B. subtilis BD 170 (stocked at The Bacillus Genetic Stock Center under BGSC No. 1A 42) and B. subtilis JH646 (stocked at The Bacillus Genetic Stock Center under BGSC No. 1S9) can also be used.

EXAMPLES

General Methods

The following methods were performed as described by Maniatis et al., supra, unless otherwise indicated:

Restriction endonuclease digestions at 37° C. (pp. 100–101); dephosphorylation with bacterial alkaline phosphatase (BAP) at 37° C. (pp. 133–134); ligation with T4 DNA ligase at 14° C. (pp. 390–391); transformation of DNA into CaCl$_2$-cells of E. coli HB101 and selection of transformants on agar plates containing LB-medium plus 100 μg/ml of ampicillin (pp. 250–251); DNA plasmid preparation (pp. 86–94); filling-in single-stranded DNA-tails with the large fragment of DNA polymerase I (Klenow fragment) at 14° C. (pp. 113–114); DNA separation and fragment purification from agarose gels (pp. 164–167); the use of synthetic DNA linkers in subcloning (pp. 392–397); and SDS/Polyacrylamide gel electrophoresis (pp. 348–349).

Transformation of DNA into cells of B. subtilis was performed as described by S. Contente and obnau, D. (Mol. Gen. Genet 167, 251-258 [1979]).

In vitro transcription with RNA polymerases of E. coli and B. subtilis was performed in 50 ul assays of the following composition; 40 mM Tris/HCl, pH 7.9, 10 mM MgCl$_2$, 0,1 mM DTT, 0,1 mM EDTA, 50–200 mM NaCl, 10% (v/v) glycerol, 150 μM ATP, GTP, CTP, 50 μM UTP, 5 uCi $^{32}$P-UTP (~3000 Ci/m mole, Amersham Buchler, Braunschweig), 0,05 p mole endonucleolytically-cleaved DNA, and 0,25 p mole RNA polymerase. Reactions were initiated by addition of RNA polymerase and allowed to proceed for between 1 and 5 mins at 37° C. Synthesized RNA was isolated by repeated ethanol precipitation and analyzed by high voltage gel electrophoresis through 0.4 mm thick 5 or 8% polyacrylamide gels containing 8M urea. Following electrophoresis, gels were dried and subjected to autoradiography using Kodak X-OMAT XAR 5 film at room temperature.

EXAMPLE 1

Construction of Shuttle Vector p602/5

Figure 1:
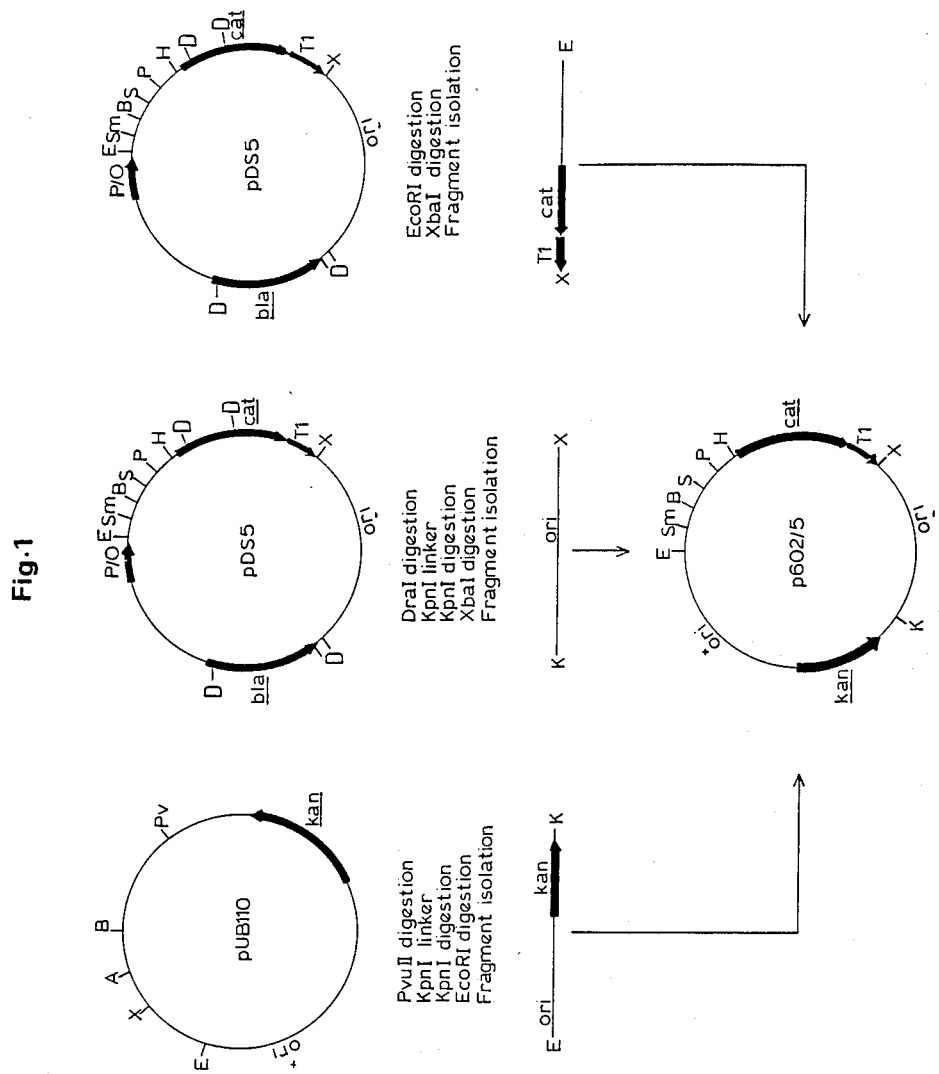

(I) Two μg of plasmid pUB110 were digested to completion with the restriction endonuclease PvuII. An octameric KpnI linker was ligated to the PvuII ends. Following ligation, the DNA was digested to completion with the endonucleases KpnI and EcoRI. The resulting digested DNA was electrophoresed through a 1% low melting temperature agarose gel containing 1 μg/ml ethidium bromide. After 2 hours of electrophoresis at 70V, the DNA bands were visualized by fluorescence, and the upper 3.5 Kb band was excised from the gel. This 3.5 Kb, EcoRI/KpnI fragment was subsequently purified from the low melting temperature agarose. (II) Five μg of plasmid pDS5 were cleaved to completion with DraI, and radioactive octameric KpnI linkers were ligated to the DraI termini. The products of ligation were subsequently cleaved to completion with the endonucleases KpnI and XbaI and separated by electrophoresis through a 6% polyacrylamide gel. A KpnI/XbaI fragment of approximately 1.2 Kb was located by autoradiography and excised from the gel. The KpnI/XbaI fragment was subsequently purified from the acrylamide gel slice. (III) Five μg of plasmid pDS5 were digested to completion with the endonucleases EcoRI and XbaI and then separated by electrophoresis through a 1% low melting temperature agarose gel containing 1 μg/ml ethidium bromide. Following electrophoresis, the DNA bands were visualized by fluorescence, and an approximately 900 bp EcoRI/SbaI fragment was excised. The EcoRI/XbaI fragment was subsequently purified from the low melting temperature agarose. (IV) Equimolar amounts of the purified DNA fragments from steps (I) to (III) were ligated, and the products of the ligation were transformed into competent cultures of E. coli strain AB1157 (Maniatis et al., supra). Transformed cells were plated on LB agar containing 10 μg/ml kanamycin. Plasmid DNA was isolated from kanamycin-resistant colonies, and the integrity of the respective fragments was verified by restriction endonuclease cleavage. The plasmid thus generated was designated p602/5. The construction of p602/5 is illustrated in FIG. 1.

EXAMPLE 2

Construction of the Expression Vector p602/7RBSI and p602/7RBSII Carrying Portable Ribosome Binding Site-encoding Synthetic DNA sequences (I) Two μg of plasmid p602/5 were digested to completion with the restriction endonucleases EcoRI and HindIII, and the approximately 5.6 Kb vector DNA fragment was isolated. This fragment was thereafter ligated with a 125 bp EcoRI/HindIII fragment containing the B. subtilis promoter PvII, having the following DNA sequence:

```
5'AATTCTCATG TTTGACAGCT TATCATCGAA TTATAGGAAT AGAGCAAACA
3'   GAGTAC AAACTGTCGA ATAGTAGCTT AATATCCTTA TCTCGTTTGT

AGCAAAGGAA ATTTTGTCAA AATAATTTTA TTGACAACGT CTTATTAACG
TCGTTTCCTT TAAAACAGTT TTATTAAAAT AACTGTTGCA GAATAATTGC

TTGATATAAT TTGCA      3'
AACTATATTA AACGTTCGA  5'
```

The ligation products were transformed into E. coli strain AB1157, and transformed cells were selected on LB agar containing 50 μg/ml chloramphenicol. Chloramphenicol-resistant colonies were analyzed to verify the insertion of promoter PvII into the plasmid p602/5. The resultant plasmid was designated p602/7. (II) Two μg of plasmid p602/7 were digested to completion with the endonuclease HindIII. The portable ribosome binding site-encoding synthetic DNA sequence SRBSI, having the sequence

was ligated into the HindIII site. The ligation products were transformed into E. coli strain AB1157, and transformed cells were selected on LB agar containing 50 ug/ml chloramphenicol. Chloramphenicol-resistant colonies were assayed for acquisition of plasmids containing the portable ribosome binding site-encoding synthetic DNA sequence SRBSI via (a) ability to synthesise a fusion CAT protein from SRBSI, and (b) restriction enzyme analysis of the recombinant plasmid, which harbours a newly acquired SphI site.

Plasmid DNA thus characterized was designated p602/7RBSI. Purified p602/7RBSI DNA was thereafter transformed into B. subtilis strain BR151, and chloramphenicolresistant colonies (in this case, colonies resistant to 10 ug/ml chloramphenicol) were assayed as mentioned in (II) a) and b) to verify the utility of SRBS I in B. subtilis.

(III) Plasmid p602/7RBSI was digested to completion with HindIII and SphI and purified from SRBSI by electrophoresis through a 1% low melting temperature agarose gel containing 1 μg/ml ethidium bromide. Following electrophoresis, the DNA was visualized by fluorescence and excised from the gel. The DNA was subsequently purified from the agarose. A portable ribosome binding site-encoding synthetic DNA sequence, designated SRBSII, and having the sequence

was ligated with HindIII/SphI cleaved p602/7RBSI DNA. E. coli strain AB1157 was transformed with this ligation mixture, and transformed cells were selected on LB agar containing 50 μg/ml chloramphenicol. Chloramphenicol-resistant colonies were assayed for the presence of SRBSII by (a) ability to synthesize a fusion CAT protein, and (b) restriction enzyme analysis of the recombinant plasmid, which harbours a new DraI site.

Plasmid DNA thus characterized was designated p602/7RBSII. Plasmid p602/7RBSII was introduced into competent cells of B. subtilis strain BR151, and transformed cells were selected on LB agar containing 10 ug/ml chloramphenicol. Chloramphenicol-resistant colonies were analyzed for the utility of SRBSII in B. subtilis as described in Step (III) a) and b). The construction of vectors p602/7RBSI and p602/7RBSII is illustrated in FIG. 2.

EXAMPLE 3

Construction of Expression Vector p602/25 Carrying the Coliphage T5 Promoter P$_G$25

(I) Two μg of plasmid p602/5 were digested to completion with the restriction endonuclease EcoRI. This DNA was thereafter ligated with equimolar amounts of a 250bp EcoRI fragment containing the coliphage T5 promoter P$_G$25 (R. Gentz, supra). The ligated products were transformed into E. coli strain AB1157, and transformed cells were selected on LB agar containing 100 μg/ml chloramphenicol. Plasmid DNA was isolated from chloramphenicol-resistant colonies and analyzed by EcoRI digestion, or DNA sequencing, for the presence of the 250bp fragment containing promoter P$_G$25. Plasmid DNA thus characterized was designated p602/25. The construction of p602/25 is illustrated in FIG. 2.

EXAMPLE 4

Construction of the Vector p25RBSI Carrying the Coliphage T5 Promoter P$_G$25 Combined with the Portable Ribosome Binding Site-encoding Synthetic DNA Sequence SRBSI (I) Two μg of plasmid p602/7RBSI were digested to completion with the restriction endonucleases HindIII and BglII and fractionated by electrophoresis through a 1% low melting temperature agarose gel containing 1 μg/ml ethidium bromide. Following electrophoresis, the DNA bands were visualized by fluorescence, and the upper, approximately 3.2 Kb band was excised. This fragment was then purified from the agarose.

(II) Two μg of plasmid p602/25 were likewise digested to completion with the restriction endonucleases HindIII and BglII and fractionated by electrophoresis through a 1% agarose gel containing ethidium bromide. The DNA bands were visualized by fluorescence and the lower, approximately 2.6 Kb band was excised and purified from the agarose.

(III) Equimolar amounts of the DNA fragments prepared through Example 4, (I) and (II) were ligated, and the ligation products were transformed into E. coli strain AB1157. Plasmid DNA was isolated from colonies resistant to 100 ug/ml chloramphenicol and analyzed from the presence of the 250 bp EcoRI band. Plasmid DNA thus characterized was designated p25RBSI. The construction of plasmid p25RBSI is illustrated in FIG. 3.

(IV) Plasmid DNA was isolated from E. coli harbouring p25RBSI and transformed into competent cultures of B. subtilis strain BR151, and transformed cells were selected on LB agar containing 10 μg/ml chloramphenicol. Plasmid DNA was isolated from chloramphenicol resistant colonies, and the structure of plasmid p25RBSI in B. subtilis was verified by restriction endonuclease analysis.

(V) B. subtilis colonies containing plasmid p25RBSI were cultivated in L-Broth containing 10 μg/ml chloramphenicol, and the total protein synthesized by these cultures was analyzed by SDS/polyacrylamide gel electrophoresis. Utilization of the coliphage T5 promoter $P_G25$ together with the synthetic ribosome binding site-encoding DNA sequence SRBSI was verified by synthesis of a fusion CAT protein, initiating in the immediate vicinity of SRBSI and terminating at the natural translational termination codon of the E. coli cat gene. The results of such an analysis are presented in FIG. 4.

EXAMPLE 5
Construction of the Vectors p25RBSII and p25*RBSII Carrying the Coliphage T5 Promoter $P_G25$ Combined with the Portable Ribosome Binding Site-encoding Synthetic DNA Sequence SRBSII (I) Two μg of plasmid p602/7RBSII were digested to completion with the restriction endonucleases HindIII and BglII, and the products were fractionated by electrophoresis through a 1% low melting temperature agarose gel containing 1 μg/ml ethidium bromide. Following electrophoresis, the DNA bands were visualized by fluorescence, and the upper, approximately 3.2 Kb band was excised and purified from the agarose.

(II) Two μg of the plasmid p602/25 were similarly digested to completion with the restriction endonucleases HindIII and BglII and fractionated by electrophoresis through a 1% low melting temperature agarose gel containing 1% ethidium bromide. Following electrophoresis, the DNA bands were visualized by fluorescence and the lower, approximately 2.6 Kb band was excised and purified from the gel. Equimolar amounts of the DNA fragments isolated through Example 5 (I) and (II) were ligated, and the ligation products were transformed into E. coli strain AB1157. Transformed cells were selected on LB agar containing 100 μg/ml chloramphenicol. Plasmid DNA was isolated from chloramphenicol resistant colonies, and the presence of both the coliphage T5 promoter $P_G25$ and the synthetic ribosome binding site-encoding DNA sequence SRBSII were verified by restriction endonuclease analysis. Plasmid DNA thus characterized was designated p25/RBSII. The construction of plasmid p25RBSII is illustrated in FIG. 3.

Protein synthesis in B. subtilis containing the vector p25RBSII is illustrated in FIG. 4. It was discovered here that the EcoRI fragment harbouring the promoter $P_G25$ contains an accessory ribosome binding site which produces a fusion protein extending to the end of the cat gene. The immediate effect is to drastically reduce the efficiency of RBSII. As a consequence, the protein reading frame from the ribosome binding site in the immediate vicinity of $P_G25$ was altered as follows, to maximize protein synthesis from SRBSII:

(IV) Two μg of plasmid p25/RBSII were digested to completion with the restriction endonuclease Hind III. The cohesive HindIII termini were converted to blunt termini by incubation with DNA polymerase Klenow fragment in the presence of all four dNTPs. Duodecameric HindIII linkers were ligated to these blunt termini, and the ligation products were digested to completion with HindIII. This DNA was fractionated by electrophoresis through a 1% low melting temperature agarose gel containing 1 μg/ml ethidium bromide. Following electrophoresis, the DNA was visualized by fluorescence, excised from the gel and purified from the agarose. This DNA was again ligated, and the ligation products were transformed into E. coli strain AB1157. Transformed cells were selected on LB agar containing 100 μg/ml chloramphenicol. Plasmid DNA was isolated from chloramphenicol resistant colonies, and the presence of the newly introduced HindIII site was verified by restriction endonuclease analysis. Plasmid DNA thus characterized was designated p25*RBSII. The construction of plasmid p25*RSII is illustrated in FIG. 3.

(V) PLasmid p25*RBSII was introduced into competent cultures of B. subtilis strain BR151, and transformed cells were selected on LB agar containing 10 μg/ml chloramphenicol. Plasmid DNA was then isolated from chloramphenicol resistant colonies and its structural identity to p25*RBSII isolated from E. coli was determined by restriction endonuclease analysis.

(VI) Individual chloramphenicol resistant colonies of B. subtilis were cultivated in L-Broth containing 10 μg/ml chloramphenicol, and total protein synthesized by these colonies was analyzed by SDS/polyacrylamide gel electrophoresis. The utilization of the coliphage T5 promoter $P_G25$, together with the synthetic ribosome binding site-encoding DNA sequence SRBSII, was verified by the synthesis of a fusion CAT protein, initiating in the immediate vicinity of SRBSII and terminating at the natural termination codon of the E. coli cat gene. The results of such an analysis are presented in FIG. 5.

EXAMPLE 6
In Vitro Analysis of E. coli Promoters with B. subtilis RNA Polymerase.

Table 1 indicates the promoters which were used. Their potential was determined by in vitro 'run-off' transcription, the results of which are presented in FIG. 6. In each case, promoter utilization by B. subtilis $\delta^{55}$ RNA polymerase was determined as a function of increasing ionic strength and compared with its efficiency when transcribed with E. coli RNA polymerase in 200 mM NaCl. Each transcription assay contained, in addition to the promoter in question, stoichiometric amounts of the B. subtilis veg promoter, previously shown to be efficiently utilized by B. subtilis $\delta^{55}$ RNA polymerase (Moran Jr. et al., Mol. Gen. Genetics 186, 339-346 [1982]).

It is clear from the data of FIG. 6 that all promoters tested are recognized by B. subtilis RNA polymerase, albeit to varying degrees. In the case of the coliphage T5 promoters $P_N26$ and $P_K28a/P_K28b'$ transcription may in fact be stronger than that from the veg promoter. Furthermore, the effect of salt concentration on promoter efficiency is clear. At 50 mM NaCl, B. subtilis RNA polymerase initiates transcription not only from the promoters in question, but also from the 'bla' and 'ori' promoters of the pBR322 vector DNA (for preliminary studies, all promoters were inserted into pBR322 derived vectors: these plasmids were subsequently cleaved to yield a constant 350 nucleotide 'bla' transcript and a variable length transcript from the coliphage T5 promoter in question). As the salt concentration is raised, promoter selection becomes clearly evident, partitioning between the veg and coliphage T5 promoters.

To test whether the results of FIG. 6 have in vivo relevance, coliphage T5 promoters, or the A1 promoter of coliphage T7, can be substituted for the $P_G25$ promoter of the vector p25*RBSII (FIG. 3), and CAT synthesis in *B. subtilis* can be determined.

EXAMPLE 7

Construction of the Vector p602/18 Carrying the Coliphage T5 Promoter $P_N25$ Combined with the Portable Ribosome Binding Site-encoded Synthetic DNA Sequence RBSII, 9A (I) Two μg of the plasmid pDS5/RBSII,9A were digested to completion with the restriction endonucleases XhoI and XbaI, and fractionated by electrophoresis through a 1% low melting temperature agarose gel containing 1 μg/ml ethidium bromide. Following electrophoresis, the DNA bands were visualized by fluorescence and the lower, approximately 1.0 Kb band was excised. This fragment was then purified from the agarose.

(II) Two μg of the plasmid p25*RBSII were likewise digested to completion with the restriction endonucleases XhoI and XbaI, and fractionated through a 1% low melting temperature agarose gel containing 1 μg/ml ethidium bromide. The bands were visualized by fluorescence, and the upper, approximately 4.6 Kb band was excised and purified from the agarose.

(III) Equimolar amounts of the DNA fragments prepared through Example 7, (I) and (II) were ligated, and the ligation products were transformed into competent cells of *B. subtilis* strain BR151. Plasmid DNA was isolated from transformed cells resistant to 10 μg/ml kanamycin and 10 ug/ml chloramphenicol and analyzed for the presence of the 1.0 Kb XhoI/XbaI fragment. The plasmid thus charcterized was designated p602/18. The construction of p602/18 is illustrated in FIG. 7.

(IV) *B. subtilis* colonies containing plasmid p602/18 were cultivated in L-Broth containing 10 μg/ml chloramphenicol, and total protein synthesized by these cultures was analyzed by SDS/polyacrylamide gel electrophoresis. Utilization of the coliphage promoter $P_N25$ together with the synthetic ribosome binding site-encoding DNA sequence RBSII, 9A, was verified by the synthesis of a fusion CAT protein, initiating in the immediate vicinity of RBSII, 9A and terminating at the natural translational termination codon of the *E. coli* cat gene. The results of such an analysis are presented in FIG. 9.

EXAMPLE 8

Construction of the Vector p602/19, Carrying the Coliphage T5 Promoter $P_N25$ Combined with the Portable Ribosome Binding Site-encoding Synthetic DNA Sequence RBSII, 3A+5A (I) Two μg of the plasmid pDS5/RBSII,3A+5A were digested to completion with the restriction endonucleases XhoI and XbaI and fractionated by electrophoresis through a 1% low melting temperature agarose gel containing 1 μg/ml ethidium bromide. Following electrophoresis, the DNA bands were visualized by fluorescence, and the lower, approximately 1.0 Kb band was excised. This fragment was then purified from the agarose.

(II) Two μg of plasmid p25*RBSII were likewise digested to completion with the restriction endonucleases XhoI and XbaI and fractionated by electrophoresis through a 1% low melting temperature agarose gel containing 1 μg/ml ethidium bromide. The DNA bands were visualized by fluorescence, and the upper, approximately 4.7 Kb band was excised and purified from the agarose.

(III) Equimolar amounts of the DNA fragments purified through Example 8, (I) and (II) were ligated, and the ligation products were transformed into competent cells of the *B. subtilis* strain BR151. Plasmid DNA was purified from transformants resistant to 10 μg/ml kanamycin and 10 ug/ml chloramphenicol and assayed for the presence of the 1.0 Kb XhoI/XbaI fragment. Plasmid DNA thus characterized was designated p602/19. The construction of p602/19 is illustrated in FIG. 7.

(IV) *B. subtilis* colonies containing plasmid p602/19 were cultivated in L-Broth containing 10 μg/ml chloramphenicol, and total protein synthesized by these cultures was analyzed by SDS/polyacrylamide gel electrophoresis. Utilization of the coliphage T5 promoter $P_N25$ together with the synthetic ribosome binding site-encoding DNA sequence RBSII, 3A+5A was verified by synthesis of a fusion CAT protein, initiating in the immediate vicinity of RBSII, 3A+5A, and terminating at the natural translation termination codon of the cat gene. The results of such an analysis are presented in FIG. 9.

EXAMPLE 9

Construction of the Vector p602/20 Carrying the Coliphage T5 Promoter $P_N25$ Combined with the Portable Ribosome Binding Site-encoding DNA Sequence RBSII (I) Two μg of the plasmid pDS8/RBSII were digested to completion with the restriction endonucleases XhoI and XbaI and fractionated by electrophoresis through a 1% low melting temperature agarose gel containing 1 μg/ml ethidium bromide. Following electrophoresis, the DNA bands were visualized by fluorescence, and the lower, approximately 2.0 Kb band was excised. The fragment was then purified from the agarose.

(II) Two μg of the plasmid p25*RBSII were likewise digested to completion with the restriction endonucleases XhoI and XbaI and fractionated by electrophoresis through a 1% low melting temperature agarose gel containing 1 μg/ml ethidium bromide. The DNA bands were visualized by fluorescence, and the upper, approximately 4.7 Kb band was excised and purified from the agarose.

(III) Equimolar amounts of the DNA fragments prepared through Example 9 (I) and (II) were ligated, and the ligation products were transformed into copetent cells of the *B. subtilis* strain BR151. Plasmid DNA was purified from transformants resistant to 10 μg/ml kanamycin and 10 ug/ml trimethoprim and analyzed for the presence of the 2.0 Kb XhoI/XbaI fragment. Plasmid DNA thus characterized was designated p602/20. The construction of p602/20 is illustrated in FIG. 8.

(IV) B. subtilis colonies containing plasmid p602/20 were cultivated in L-Broth containing 10 µg/ml kanamycin, and total protein synthesized by these cultures was analyzed by SDS/polyacrylamide gel electrophoresis. Utilization of the coliphage T5 promoter $P_N25$ together with the synthetic ribosome binding site-encoding DNA sequence RBSII was verified by the synthesis of a fusion DHFR protein, initiating in the immediate vicinity of RBSII and terminating at the natural translational termination codon of the dhfr gene. The results of this analysis are presented in FIG. 9.

EXAMPLE 10

Construction of the Vector p602/21 Containing the Coliphage T5 Promoter $P_N25$ Combined with the Portable Ribosome Binding Site-encoding DNA Sequence RBSII, 3A+5A (I) Two µg of the plasmid pDS8/RBSII, 3A+5A were digested to completion with the restriction endonucleases XhoI and XbaI, and the products were fractionated through a 1% low melting temperature agarose gel containing 1 µg/ml ethidium bromide. Following electrophoresis, the DNA bands were visualized by fluorescence, and the lower, approximately 2.0 Kb band was excised and purified from the agarose.

(II) Two µg of the plasmid p25*RBSII were likewise digested to completion with the restriction endonucleases XhoI and XbaI, and the products were fractionated through a 1% low melting temperature agarose gel containing 1 µg/ml ethidium bromide. Following electrophoresis, the DNA bands were visualized by fluorescence, and the lower, approximately 2.0 Kb band was excised and purified from the agarose.

(III) Equimolar amounts of the DNA fragments purified through Example 10 (I) and (II) were ligated, and the ligation products were transformed into competent cells of the B. subtilis strain BR151. Plasmid DNA was isolated from transformants resistant to 10 µg/ml kanamycin and 10 ug/ml trimethoprim and assayed for the presence of the 2.0 Kb XhoI/XbaI fragment. Plasmid DNA thus characterized was designated p602/21. The construction of p602/21 is illustrated in FIG. 8.

(IV) B. subtilis colonies containing plasmid p602/21 were cultivated in L-Broth containing 10 µg/ml kanamycin, and total protein synthesized by these cultures was analyzed by SDS/polyacrylamide gel electrophoresis. Utilization of the coliphage T5 promoter $P_N25$ together with the synthetic ribosome binding site-encoding DNA sequence RBSII, 3A+5A was verified by the synthesis of a fusion DHFR protein, initiating in the immediate vicinity of RBSII, 3A+5A and terminating at the natural termination codon of the dhfr gene. The results of such an analysis are presented in FIG. 9.

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. A DNA sequence containing transcriptional and translational control elements functional in a B. subtilis bacterium, comprising in the downstream direction of transcription:
 (a) a coliphage T5 or T7 promoter;
 (b) a sequence of a synthetic oligonucleotide selected from the group consisting of SRBSI; SRBSII; RBSII, 3A+5A; RBSII and RBSII, 9A, which sequence functions as a ribosome binding site; and
 (c) a transcription termination sequence selected from the group consisting of the $t_0$, T1, T2 and T7 terminator.

2. The DNA sequence of claim 1 in which the sequence of the synthetic oligonucleotide is operatively linked to a foreign gene encoding a prokaryotic or eukaryotic polypeptide.

3. The DNZ sequence of claim 2 in which the coliphage T5 promoter is selected from the group consisting of the $P_{N25}$, $P_{N26}$, $P_{G25}$, $P_{J5}$, $P_{D/E20}$, $P_{K28a}$ and $P_{K28b}$ promoter.

4. The DNZ sequence of claim 2 in which the coliphage T7 promoter is selected from the group consisting of the T7A1 and T7A2 promoter.

5. An expression vector capable of functioning in a B. subtilis bacterium, comprising:
 (a) A DNA sequence containing transcriptional and translational control elements functional in a B. subtilis bacterium, comprising in the downstream direction of transcription:
  (i) a coliphage T5 or T7 promoter;
  (ii) a sequence of a synthetic oligonucleotide selected from the group consisting of SRBSI; SRBSII; RBSII, 3A+5A; RBSII and RBSII, 9A, which sequence functions as a ribosome binding site; and
  (iii) a transcription termination sequence selected from the group consisting of the $t_0$, T1, T2 and T7 terminator;
 (b) at least one vector origin of replication; and
 (c) at least one antibiotic resistance gene.

6. The expression vector of claim 5 in which the sequence of the synthetic oligonucleotide is operatively linked to a foreign gene encoding a prokaryotic or eukaryotic polypeptide.

7. The expression vector of claim 6 which is a plasmidic shuttle vector capable of replication in an E. coli and B. subtilis bacterium.

8. The expression vector of claim 7 which is selected from the group consisting of p25RBSI, p25RBSII and p25*RBSII.

9. The expression vector of claim 7 which is selected from the group consisting of p602/18, p602/19, p602/20 and p602/21.

10. A B. subtilis transformant carrying the expression vector of claim 6.

11. The transformant of claim 10 which is Bacillus subtilis strain BR 151.

12. A process for producing the DNA sequence of claim 2, which process comprises combining in the downstream direction of transcription:

(a) a coliphage T5 or T7 promoter;
(b) a sequence of a synthetic oligonucleotide selected from the group consisting of SRBSI; SRBSII; RBSII, 3A+5A; RBSII and RBSII, 9A, which sequence functions as a ribosome binding site and is operatively linked to a foreign gene encoding a prokaryotic or eukaryotic polypeptide; and
(c) a transcription termination sequence selected from the group consisting of the $t_0$, T1, T2 and T7 terminator, to produce a functional unit.

13. A process for producing the expression vector of claim 6, which process comprises:
(a) inserting into an existing cloning vector in the downstream direction of transcription at least one coliphage T5 or T7 promoter and a sequence of a synthetic oligonucleotide selected from the group consisting of SRBSI; SRBSII; RBSII, 3A+5A; RBSII and RBSII, 9A, which sequence functions as a ribosome binding site;
(b) providing in the cloning vector at least one restriction endonuclease site next to the synthetic oligonucleotide sequence;
(c) inserting at least one foreign gene encoding a prokaryotic or eukaryotic polypeptide into the restriction endonuclease site; and
(d) inserting at least one transcription termination sequence selected from the group consisting of the $t_0$, T1, T2 and T7 terminator in the downstream direction of the foreign gene.

14. A process for producing a prokaryotic or eukaryotic polypeptide, which process comprises:
(a) culturing the transformant of claim 10 under conditions in which the foreign gene encoding the polypeptide is expressed; and
(b) isolating the polypeptide from the culture.

15. The process of claim 14 in which the vector is a plasmidic shuttle vector capable of replication in an *E. coli* and *B. subtilis* bacterium.

16. The process of claim 15, in which the shuttle vector is selected from the group consisting of p25RBSI, p25RBSII and p25*RBSII.

17. The process of claim 15 in which the shuttle vector is selected from the group consisting of p602/18, p602/19, p602/20 and p602/21.

18. The process of claim 14 in which the polypeptide is E. coli chloramphenicol acetyltransferase.

19. The process of claim 14 in which the polypeptide is mouse dihydrofolate reductase.

20. A synthetic oligonucleotide comprising a nucleotide sequence which functions as a ribosome binding site in a *B. subtilis* bacterium and is selected from the group consisting of SRBSI; SRBSII; RBSII, 3A+5A; RBSII and RBSII, 9A.

* * * * *

UNITED STATES PATENT AND TRADEMARK OFFICE
CERTIFICATE OF CORRECTION

PATENT NO.  : 4,868,111

DATED       : Sept. 19, 1989

INVENTOR(S) : Hermann Bujard, Stuart LeGrice

It is certified that error appears in the above-identified patent and that said Letters Patent is hereby corrected as shown below:

Column 20, Line 22, "DNZ" should be: DNA

Column 20, Line 26, "DNZ" should be: DNA

Signed and Sealed this

Second Day of October, 1990

*Attest:*

HARRY F. MANBECK, JR.

*Attesting Officer*  *Commissioner of Patents and Trademarks*